United States Patent [19]

Taverne et al.

[11] Patent Number: 5,234,924
[45] Date of Patent: Aug. 10, 1993

[54] BENZOTHIAZINE AND BENZOTHIAZOLE COMPOUNDS USEFUL AS ANALGESICS

[75] Inventors: Thierry Taverne, Saint Martin les Boulogne; Isabelle Lesieur, Gondecourt; Patrick Depreux, Armentieres; Daniel H. Caignard, Paris; Béatrice Guardiola, Neuilly-sur-Seine; Gérard Adam, Le Mesnil le Roi; Pierre Renard, Versailles, all of France

[73] Assignee: Adir et Compagnie, Courbevoie, France

[21] Appl. No.: 802,503

[22] Filed: Dec. 5, 1991

Related U.S. Application Data

[63] Continuation-in-part of Ser. No. 766,038, Sep. 26, 1991, abandoned.

[30] Foreign Application Priority Data

Sep. 26, 1990 [FR] France ............... 90 11866

[51] Int. Cl.$^5$ ............... A61K 31/54; A61K 31/495; C07D 279/16; C07D 403/00
[52] U.S. Cl. ............... 514/224.2; 514/233.8; 514/253; 544/135; 544/52; 544/295; 544/368
[58] Field of Search ............... 544/52, 135, 295, 368; 514/224.2, 233.8, 255, 253

[56] References Cited

U.S. PATENT DOCUMENTS

| | | | |
|---|---|---|---|
| 4,033,951 | 7/1977 | Maisey | 544/52 |
| 4,554,284 | 11/1985 | Stringer et al. | 548/211 |
| 4,640,916 | 2/1987 | Meguro | 514/222 |
| 4,831,031 | 5/1989 | Lowe, III et al. | 544/359 |
| 4,914,094 | 4/1990 | Oshiro et al. | 514/213 |
| 4,931,443 | 7/1990 | Nakao et al. | 514/252 |
| 5,096,482 | 3/1992 | Kume | 544/52 |

FOREIGN PATENT DOCUMENTS 0047784 2/1989 Japan.

OTHER PUBLICATIONS

Lowe III, et al., Journal of Medicinal Chemistry (1991) 34 1860–1866.
Chemical Abstracts 115:8728g (1991).
Chemical Abstracts 110:39024a (1988).
Chemical Abstracts 111:15384z (1989).

*Primary Examiner*—Mukund J. Shah
*Assistant Examiner*—Matthew V. Grumbling
*Attorney, Agent, or Firm*—Gordon W. Hueschen

[57] ABSTRACT

Compound of general formula (I):

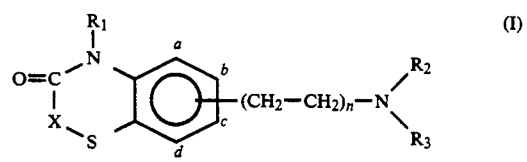

where $R_1$, $R_2$, $R_3$, n and X are defined in the description. Medicinal products.

23 Claims, No Drawings

BENZOTHIAZINE AND BENZOTHIAZOLE COMPOUNDS USEFUL AS ANALGESICS

The present application is a continuation-in-part of our prior-filed co-pending U.S. application Ser. No. 07/766,038, filed Sep. 26, 1991, now abandoned.

The present invention relates to new heterocycle-substituted piperazines, to a process for preparing these and to pharmaceutical compositions containing them.

Some piperazinyl alkyl benzothiazolinonyl compounds have already been disclosed in the European Patent Application EP 0281309. The pharmacological results of these compounds have been recently published in J. Med. Chem., 1991, 34, 6, 1860–1866 and it appears that such compounds are potential atypical antipsychotic agents. This activity seems due to a high affinity to both serotoninergic and dopaminergic receptors. However it is well known that exist various subclasses of serotoninergic receptors, the most well known being 5HT1A, 5HT1B, 5HT2, 5HT3. It also exists various subclasses of dopaminergic receptors D1, D2 etc.

The pharmacological results of compound of European Patent 0281309 published in J. Med. Chem. 1991, 34, 4, 1860–1866 mainly indicate the binding to $5HT_1A$, $5HT_2$ and $D_2$ receptors. It is well known elsewhere that the pharmacological effects obtained when stimulation these two $5HT_1A$ and $5HT_2$ receptors are mainly the opposite ones. So, according to the publication J. Med. Chem. 1991, 34, 6, 1860–1866, it is suitable to obtain the stimulation of the $5HT_1A$ receptors (agonism) without the stimulation of $5HT_2$ receptors (antagonism), but the publication does not indicate if the compounds are agonists or antagonists of $5HT_2$ receptors.

Another way of obtaining compounds without such an inconvenient is to obtain compounds binding to $5HT_1A$ receptors without binding to $5HT_2$ receptors.

Surprisingly our compounds bind both to $5HT_1A$ and $D_2$ receptors with an affinity which is a little better than compounds of European Patent Application EP 0281309 but, overall with a much greater selectivity concerning 5HT2 receptors. The selectivity of binding to $5HT_1A$ receptors in comparison with $5HT_2$ receptors is about for our compounds from 10 to 30 fold greater than for compounds of European Patent Applications EP 0281309.

The very high affinity and selectivity of the compounds of the invention for $5HT_1A$ serotoninergic receptors render them usable in the treatment of diseases of the serotoninergic system, and more especially depression, stress, anxiety and schizophrenia, at lower doses than the compounds of the prior art. This feature, combined with their low toxicity, renders the compounds of the invention usable with much greater safety than the compounds of the prior art, which is especially advantageous in view of the frailty of the populations at which this type of treatment is aimed.

More specifically, the present invention relates to the compounds of general formula (I):

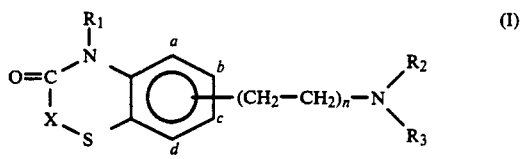

in which:
$R_1$ represents hydrogen or lower alkyl,
n represents 1 or 2,
X represents $CH_2$ or a single bond,
$R_2$ and $R_3$ together with the nitrogen atom which carries them, form a mono- or bicyclic heterocyclic system, each ring being five- or six-membered and optionally including in its carbon skeleton one or two hetero atoms selected from nitrogen, oxygen and sulfur, said ring being unsubstituted or substituted on a nitrogen atom present with a lower alkyl, phenyl, phenyl (lower alkyl), pyridyl, or pyrimidinyl group, or a phenyl group substituted with one or more lower alkyl, trifluoromethyl, or lower alkoxy groups or halogen atoms, or phenyl (lower alkyl) group substituted on the phenyl ring with one or more lower alkyl, trifluoromethyl or lower alkoxy groups or halogen atoms, or a pyridyl group substituted with one or more lower alkyl, trifluoromethyl or lower alkoxy groups or halogen atoms, their enantiomers, diastereoisomers and epimers as well as their addition salts with a pharmaceutically acceptable acid or a pharmaceutically acceptable base when $R_1 = H$.

Among pharmaceutically acceptable acids, hydrochloric, sulfuric, tartaric, maleic, fumaric, oxalic, methanesulfonic, camphoric, ethanesulfonic and citric acids, and the like, may be mentioned without implied limitation. Among pharmaceutically acceptable bases, sodium, potassium and calcium hydroxides, as well as sodium, potassium and calcium carbonates, and the like, may be mentioned without implied limitation.

The invention also encompasses the process for preparing the compounds of general formula (I), wherein a derivative of formula (II):

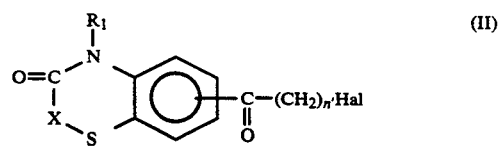

with Hal representing a halogen atom and $R_1$ and X having the same definition as in the formula (I), and n' represents 1 or 3, is used as a starting material, which compound is treated with a trialkylsilane in an acid medium to yield a compound of formula (III):

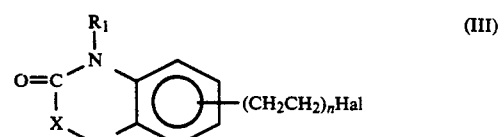

with X, $R_1$, n and Hal as defined above, which is condensed with an amine of formula:

with R₂ and R₃ having the same definition as above, to yield a compound of formula (I):

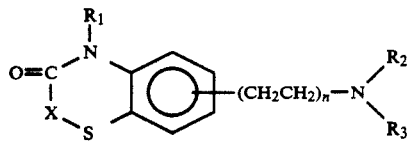

with $R_1$, X, n, $R_2$ and $R_3$ having the same definition as above, the isomers of which are separated, where appropriate, and purified if necessary by chromatography or crystallization, which compound of formula (I) may be, if so desired, salified with a pharmaceutically acceptable acid.

The compounds of formula (I) possess advantageous pharmacological properties.

Binding tests showed that the compounds of the invention behave as very potent ligands of 5-HT$_1$A receptors. This affinity is accompanied by a very great selectivity with respect to other receptors, in particular 5HT$_2$, in contrast to the behavior observed with the compounds of the prior art.

The compounds of the invention are of low toxicity, and possess good activity in the pigeon conflict test, confirming the activity detected by binding.

The compounds of the invention hence find their application in the treatment of distress, anxiety, depression, schizophrenia, psychoses, dementia, senile dementia, aggressiveness, agitation and disorders.

The subject of the present invention is also pharmaceutical compositions containing as active principle at least one compound of general formula (I) or one of its addition salts with a pharmaceutically acceptable acid or, where appropriate, with a pharmaceutically acceptable base, alone or in combination with one or more non-toxic, inert excipients or vehicles.

Among the pharmaceutical compositions according to the invention, there may be mentioned, more especially, those which are suitable for oral, parenteral or nasal administration, simple or sugar-coated tablets, sublingual tablets, sachets, packets, hard gelatin capsules, sublingual preparations, troches, suppositories, creams, ointments, skin gels, and the like.

The dosage varies according to the patient's age and weight and the nature and severity of the condition, as well as the administration route. The latter may be oral, nasal, rectal or parenteral.

Generally speaking, single doses range between 0.05 and 30 mg for conditions affecting mental behavior and between 1 mg and 500 mg for the treatment of pain and of arterial hypertension, that is to say, taken in one to three doses per 24 hours.

The examples which follow illustrate the invention and in no way limit the latter.

The 1H nuclear magnetic resonance spectra were recorded using TMS (tetramethylsilane) as an internal reference. The chemical shifts are expressed in parts per million (ppm). The infrared spectra were run in the form of a potassium bromide disk containing approximately 1% of the product to be analyzed.

The preparations do not form part of the invention, but are useful for carrying out the synthesis of the compounds of the invention.

PREPARATION 1

6-(Bromoacetyl)Benzothiazolinone 210 g (1.60 mol) of aluminum chloride are introduced into a 500-cm³ ground-necked flask surmounted by a condenser, and 43 cm³ of dimethylformamide are then added dropwise and with magnetic stirring via a dropping funnel. 30.2 g (0.2 mol) of benzothiazolinone are then added and, while the reaction medium homogenizes, the temperature is stabilized at 70° C. using an oil bath. 19.8 cm³ (0.24 mol) of bromoacetyl chloride are then introduced gradually. After the addition, the mixture is left stirring for one hour at a temperature of 70° C. The reaction medium is hydrolyzed by pouring it onto crushed ice and the precipitate obtained is drained, washed copiously with water and dried. The product is recrystallized in dioxane.

Yield: 65%.

Melting point: 235° C. with decomposition.

PREPARATION 2

6-(2-Bromoethyl)Benzothiazolinone

In a 500-cm³ ground-necked flask surmounted by a condenser, and placed in an oil bath, 40.8 g (0.15 mol) of 6-(bromoacetyl)benzothiazolinone are dissolved in 90 cm³ of trifluoroacetic acid with magnetic stirring and while the temperature is stabilized at 60° C. 52.7 cm³ (0.33 mol) of triethylsilane are introduced dropwise via a dropping funnel. After the addition, the heating is stopped and the mixture is then left stirring vigorously for 30 hours. The reaction medium is hydrolyzed by pouring it into ice-cold water, and the precipitate obtained is drained and washed with water until the filtrate is neutral and then with hexane. The product is dried and recrystallized in absolute ethanol.

Yield: 80%.

Melting point: 179°-180° C.

PREPARATION 3

3-Methylbenzothiazolinone

In a 2-liter flask, 75.6 g (0.5 mol) of benzothiazolinone are dissolved in a solution containing 20 g of sodium hydroxide (0.5 mol) in approximately 800 cm³ of water. The solution is filtered. With magnetic stirring, 47.5 cm³ of methylsulfate (0.5 mol) are introduced drop-wise with a dropping funnel. After the addition, the mixture is left stirring for 20 hours at room temperature. The medium is alkalinized with a slight excess of sodium hydroxide and left stirring for one hour. The precipitate obtained is drained and washed with water until the filtrate is neutral. The product is dried. It is recrystallized in propanol.

Yield: 88%.

Melting point: 72°-74° C.

PREPARATION 4

3-Methyl-6-(Bromoacetyl)Benzothiazolinone 210 g (1.60 mol) of aluminum chloride are introduced into a 500-cm³ ground-necked flask surmounted by a condenser, and 43 cm³ of dimethylformamide are then added dropwise and with magnetic stirring via a dropping funnel. 33 g (0.20 mol) of 3-methylbenzothiazolinone are then added and, while the reaction medium homogenizes, the temperature is stabilized at 70° C. using an oil bath. 19.8 cm³ (0.24 mol) of bromoacetyl chloride are then added gradually. After the addition, the mixture is left stirring for one hour at a temperature of 70° C. The reaction medium is hydrolyzed by pouring it onto crushed ice and the precipitate obtained is drained, washed with water until the filtrate is neutral and dried. The product is recrystallized in 95° strength alcohol.

Yield: 66%.

Melting point: 164°–165° C.

PREPARATION 5

3-Methyl-6-(2-Bromoethyl)Benzothiazolinone

In a 500-cm³ ground-necked flask surmounted by a condenser and placed in an oil bath, 42.9 g (0.15 mol) of 3-methyl-6-(bromoacetyl)benzothiazolinone are dissolved in 77 cm3 of trifluoroacetic acid with magnetic stirring and while the temperature is stabilized at 60° C. 52.7 cm³ (0.33 mol) of triethylsilane are introduced dropwise via a dropping funnel. After the addition, the heating is stopped and the mixture is left stirring vigorously for 30 hours. The reaction medium is hydrolyzed by pouring it into ice-cold water, and the precipitate obtained is drained and washed with water until the filtrate is neutral and then with hexane. The product is dried and recrystallized in cyclohexane.

Yield: 86%.

Melting point: 97°–98° C.

PREPARATION 6

7-(Bromoacetyl)Benzothiazinone 0.01 mol of 7-acetylbenzothiazinone, described in Am. Chem. Rome, is dissolved in 100 cm³ of methylene chloride. 0.011 mol of bromine is added dropwise and with stirring via a dropping funnel, and stirring is maintained for 13 hours. The mixture is filtered and evaporated to dryness and the residue is recrystallized.

PREPARATION 7

7-(2-Bromoethyl)-3-Oxo-2,3-Dihydro-1,4-Benzothiazine

This product is advantageously obtained either by catalytic hydrogenation of 7-(bromoacetyl)-3-oxo-2,3-dihydro-1,4-benzothiazine, in an acetic acid medium in the presence of palladinized charcoal, or by the action of trialkylsilane on this compound in a trifluoroacetic acid medium.

PREPARATION 8

6-(4-Bromobutyl)Benzothiazolinone

Using the procedure described in Preparation 2, but replacing 6-(bromoacetyl)benzothiazolinone by 6-(4-bromobutyryl)benzothiazolinone, the product of the title is obtained.

PREPARATION 9

3-Methyl-6-(4-Bromobutyl)Benzothiazolinone

Using the procedure described in Preparation 5, but replacing 6-(bromoacetyl)-3-methylbenzothiazolinone by 3-methyl-6-(4-bromobutyryl)benzothiazolinone, the product of the title is obtained.

EXAMPLE 1

3-Methyl-6-{2-[4-(2,3,4-Trimethoxybenzyl)-1-Piperazinyl])-Ethyl}Benzothiazolinone Dihydrochloride 5.4 g (0.02 mol) of 3-methyl-6-(2-bromoethyl)benzothiazolinone, dissolved beforehand in 150 cm³ of dioxane, followed by 5.9 g (0.022 mol) of trimetazidine and 1 g of triethylamine (0.01 mol), are introduced into a 250-cm³ ground-necked flask equipped with a reflux condenser. The mixture is heated to reflux with magnetic stirring for 96 hours. After cooling, the reaction mixture is drained and the filtrate is then evaporated on a water bath under vacuum. The residue is taken up with 5% HCl solution. The acidic aqueous phase is washed with ethyl acetate and then alkalinized with 10% sodium hydroxide solution. It is extracted with ether and the organic phase is washed with distilled water and then dried over calcium chloride. The organic phase is filtered and evaported to dryness on a water bath under vacuum. The residue is taken up in absolute ethanol, a stream of gaseous HCl is bubbled through and the product is drained and then dried. It is recrystallized in methanol.

Yield: 52%.

Melting point: 242° C.

Molecular weight: 530.52 g/mol.

| Percentage composition: | | | | |
|---|---|---|---|---|
| Calculated | C 54.34 | H 6.27 | N 7.92 | Cl 13.37 |
| Found | C 53.80 | H 6.20 | N 7.79 | Cl 13.35 |

Infrared spectrometry: 3050–2800 cm$^{-1}$:v (C—H) 2700–2100 cm$^{-1}$:v (NH+) 1680 cm$^{-1}$:v (C=O) —S—CO—N— 1600–1580 cm$^{-1}$:v (C=C) aromatic.

Nuclear Magnetic Resonance spectrometry: Solvent: DMSO-d$_6$

δ=3.14 to 3.61 ppm unresolved peaks; (12H) CH$_2$—CH$_2$—N and piperazine

δ=3.39 ppm singlet; (3H) 1 NCH$_3$

δ=3.75–3.81–3.86 ppm singlets; (3×3H) OCH$_3$

δ=4.19 ppm singlet; (2H) N(CH2)-trimethoxybenzyl

δ=6.75 to 7.56 ppm multiplet; (5H) aromatic

δ=11,75 ppm signal; (2H) (NH+)

EXAMPLES 2 TO 4

3-METHYL-6-[2-(4-ARYL-1-PIPERAZINYL)-ETHYL]BENZOTHIAZOLINONE 5.4 g (0.02 mol) of 3-methyl-6-(2-bromoethyl)benzothiazolinone, dissolved beforehand in 150 cm³ of dioxane and 0.022 mol of 4-arylpiperazine, are introduced into a 250 cm³ ground-necked flask equipped with a reflux condenser. The mixture is heated to reflux with magnetic stirring for 96 hours.

The reaction mixture is evaporated on a water bath under vacuum and the residue is rinsed with 5% HCl solution and then with distilled water, drained and washed with ethyl acetate. The product is dried and recrystallized. The purification is slightly different if the desired product is the basic form.

EXAMPLE 2

3-Methyl-6-{2-[4-(3-Trifluoromethylphenyl)-1-Piperazinyl] Ethyl}Oromethylphenyl)-1-Piperazinyl) Ethyl) Benzothiazolinone Monohydrochloride Recrystallization Solvent: propanol or ethanol.
Yield: 50%.
Melting point: 236°–237° C.
Molecular weight: 457.96 g/mol.

| Percentage composition: | | | | |
|---|---|---|---|---|
| Calculated | C 55.08 | H 5.06 | N 9.18 | Cl 7.74 |
| Found | C 54.98 | H 5.12 | N 9.03 | Cl 7.81 |

Infrared spectrometry: 3100–2800 cm$^1$: v (C—H) 2700–2300 cm$^{-1}$: v (NH+) 1680 cm$^{-1}$: v (C=O) —S—Co—N— 1600–1580 cm$^{-1}$: v (C=C) aromatic Nuclear Magnetic Resonance spectrometry: Solvent: DMSO-d$_6$ $\delta$ = 3.21 to 3.84 ppm unresolved peaks; (12H) -CH$_2$
$\delta$ = 3.39 ppm singlet : (3H) : NCH$_3$
$\delta$ = 7.05 to 7.53 ppm multiplet; (7H) aromatic
$\delta$ = 11.32 ppm signal; (1H) (NH+)

EXAMPLE 3

3-Methyl-6-{2-[4-(2-Methoxyphenyl)-1-Piperazinyl]Ethyl}-Benzothiazolinone Monohydrochloride Recrystallization solvent: methanol.
Yield: 55%.
Melting point: >250° C.
Molecular weight: 419.98 g/mol.

| Percentage composition: | | | | |
|---|---|---|---|---|
| Calculated | C 60.06 | H 6.24 | N 10.01 | Cl 8.44 |
| Found | C 60.15 | H 6.24 | N 09.88 | Cl 8.68 |

Infrared spectrometry: 3000–2800 cm$^{-1}$: v (C—H) 2750–2400 cm$^{-1}$: v (NH+) 1680 cm$^{-1}$: v (C=O) —S—CO—NR— 1600–1580 cm$^{-1}$: v (C=C) aromatic Nuclear Magnetic Resonance spectrometry: Solvent: DMSO-d$_6$ $\delta$ = 3.07 to 3.63 ppm unresolved peaks; (12H) —CH$_2$
$\delta$ = 3.42 ppm singlet; (3H) ; NCH$_3$
$\delta$ = 3.84 ppm singlet; (3H) OCH$_3$
$\delta$ = 6.93 to 7.59 ppm multiplet; (7H) aromatic
$\delta$ = 11.31 ppm signal; (1H) (NH+)

EXAMPLE 4

3-Methyl-6-{2-[4-(4-Fluorophenyl)-1-Piperazinyl]Ethyl}-Benzothiazolinone Dihydrochloride Recrystallization solvent: methanol.
Yield: 45%.
Melting point: 234°–235° C.
Molecular weight: 444.41 g/mol.

| Percentage composition: | | | | |
|---|---|---|---|---|
| Calculated | C 54.05 | H 5.44 | N 9.45 | Cl 15.96 |
| Found | C 54.11 | H 5.45 | N 9.48 | Cl 15.81 |

Infrared spectrometry: 3100–2800 cm$^{-1}$: v (C—H) 2700–2100 cm$^{-1}$: v (NH+) 1680 cm$^{-1}$: v (C=O) —O—CO—NR— 1600–1580 cm$^{-1}$: v (C=C) aromatic Nuclear Magnetic Resonance spectrometry: Solvent: DMSO-d$_6$ $\delta$ = 3.26 to 3.82 ppm unresolved peaks; (12H) —CH$_2$
$\delta$ = 3.42 ppm singlet; (3H); NCH$_3$
$\delta$ = 6.65 to 7.61 ppm multiplet; (7H) aromatic
$\delta$ = 11.82 ppm signal; (2H) (NH+)

EXAMPLE 5

6-{2-4-(3-Trifluoromethylphenyl)-1-Piperazinyl]Ethyl}-Benzothiazolinone 5.2 g (0.02 mol) of 6-(2-bromoethyl)benzothiazolinone, dissolved beforehand in 150 cm$^3$ of dioxane, followed by 0.022 mol of 1-(3-trifluoromethylphenyl) piperazine and 0.2 g of potassium iodide, are introduced into a 250-cm$^3$ ground-necked flask equipped with a reflux condenser. The mixture is heated to reflux with magnetic stirring for 96 hours.

The reaction mixture is evaporated on a water bath under vacuum and the precipitate is ground in 5% HCl solution, drained and washed with water. The precipitate is taken up in 10% aqueous Na$_2$CO$_3$ solution and extracted with ethyl acetate; the organic phase is washed with water and the solvent is then evaporated off. The residue is dissolved in a minimum amount of ethanol and a stream of gaseous hydrogen chloride is bubbled through; the precipitate is then drained. The precipitate is taken up in water containing 2 equivalents of K$_2$CO$_3$ and the mixture is stirred for 1 to 2 hours. The precipitate is drained and washed with distilled water. The product is dried and recrystallized in propanol.

Yield: 45%.
Melting point: 132° C.
Molecular weight: 407.47 g/mol.

| Percentage composition: | | | |
|---|---|---|---|
| Calculated | C 58.95 | H 4.95 | N 10.31 |
| Found | C 59.02 | H 4.76 | N 10.28 |

Infrared spectrometry:
3160 cm$^{-1}$: v (N—H)
3100–2800 cm$^{-1}$: v (C—H) —CH$_2$—
1680 cm$^{-1}$: v (C=O) —S—CO—NR—
1600–1580 cm$^{-1}$: v (C=C) aromatic Nuclear Magnetic Resonance spectrometry: Solvent: DMSO-d$_6$ $\delta$ = 2.39 to 3.51 ppm unresolved peaks; (12H) —CH$_2$
$\delta$ = 6.96 to 7.57 ppm multiplet; (7H) aromatic
$\delta$ = 11.75 ppm signal; (1H) —NH—

Using the procedure described in examples 1 to 4 but replacing 3-methyl-6-(2-bromoethyl)benzothiazolinone by 3-methyl-6-(4-bromo butyl) benzothiazolinone, the following are obtained:

EXAMPLE 6

3-Methyl-6-{4-[4-(2,3,4-Trimethoxybenzyl)-1-Piperazinyl]-Butyl}Benzothiazolinone Dihydrochloride

EXAMPLE 7

3-Methyl-6-{4-[4-(3-Trifluoromethylphenyl)-1-Piperazinyl]-Butyl}Benzothiazolinone Monohydrochloride Melting point: 182°–184° C.

EXAMPLE 8

3-Methyl-6-{4-[4-(2-Methoxyphenyl)-1-Piperazinyl]-Butyl} Benzothiazolinone Monohydrochloride Recrystallized in toluene.
Melting point: 203°-232° C.

EXAMPLE 9

3-Methyl-6-{4-[4-(4-Fluorophenyl)-1-Piperazinyl]-Butyl}Benzothiazolinone

EXAMPLE 10

6-{4-[4-(2-Methoxyphenyl)-1-Piperazinyl]Butyl}Benzothiazolinone

Using the procedure described in Example 3, but replacing 3-methyl 6-(2-bromoethyl)benzothiazolinone by 6-(4-bromobutyl)benzothiazolinone and without acidification at the end of synthetis, the product of the title is obtained.
Melting point: 125°-127° C.

EXAMPLE 11

6-{2-[4-(Methoxyphenyl)-1-Piperazinyl]Ethyl} Benzothiazolinone, Hydrochloride

Using the procedure described in Example 5 but replacing 1-(3-trifluoromethyl phenyl) piperazine by 1-(2-methoxy phenyl) piperazine and isolating the hydrochloride at the end of the synthesis (no alcalinisation using $K_2CO_3$), the product of the title is obtained. Recrystallisation in water.
Melting point: >260° C.

EXAMPLE 12

7-{2-[4-(3-Trifluoromethyl Phenyl)-1-Piperazinyl]Ethyl}2,3-Dihydro 3-Oxo 1,4 Benzothiazine Using the procedure described in Example 5 but replacing 6-(2-bromoethyl)benzothiazolinone by 7-(2-bromoethyl) 2,3-dihydro 3-oxo 1,4-benzothiazine (obtained using 7-acetyl 2,3-dihydro 3-oxo 1,4-benzothiazine (described in Ann. Chem. Rome, 1955, 45, 172) treated with bromine in methylene chloride to give 7-bromoacetyl 2,3-dihydro 3-oxo 1,4-benzothiazine, then by triethysilane in acidic medium to give 7-(2-bromoethyl)2,3-dihydro 3-oxo 1,4-benzothiazine, the product of the title is obtained.

EXAMPLE 13

3-Methyl 6-{2-[4-(3-Pyridyl)-1-Piperazinyl]Ethyl}Benzothiazolinone, Hydrochloride Using the procedure described in Example 2 but replacing 1-(3-trifluoromethyl phenyl) piperazine by 1-(3-pyridyl) piperazine, the product of the title is obtained.

EXAMPLE 14

3-Methyl 6-{2-[4-(2-Pyrimidyl)-1-Piperazinyl]Ethyl} Benzothiazolinone, Hydrochloride Using the procedure described in example 2 but replacing 1-(3-trifluoromethyl phenyl) piperazine by 1-(2-pyrimidyl)piperazine, the product of the title is obtained.

EXAMPLE 15

3-Methyl 6-{2-[4-(2-Pyridyl)-1-Piperazinyl]Ethyl}Benzothiazolinone, Hydrochloride Using the procedure described in example 2 but replacing 1-(3-trifluoromethyl phenyl) piperazine by 1-(2-pyridyl) piperazine, the product of the title is obtained.

EXAMPLE 16

8-{2-[4-(3-Trifluoromethyl Phenyl)Piperazin-1-YL]Ethyl} 2,3-Dihydro 3-Oxo 1,4 Benzothiazine Using the procedure described in example 12 but replacing 7-(2-bromoethyl)2,3-dihydro 3-oxo 1,4-benzothiazine by 8-(2-bromoethyl)2,3-dihydro 3-oxo 1,4-benzothiazine (obtained using as starting material 8-acetyl 2,3-dihydro 3-oxo 1,4-benzothiazine described in Eur. J. Med. Chem. 1989,24(5), 479-484), the product of the title is obtained.

EXAMPLE b 17

6-{4-[4-(3- Trifluoromethyl Phenyl))-1-Piperazinyl)Butyl)} Benzothiazolinone

Using the procedure described in Example 5 but replacing 6-(2-bromoethyl)benzothiazolinone by 6-(4-bromobutyl) benzothiazolinone, the product of the title is obtained.
Recrystallization in 95° strength alcohol.
Melting point: 129°-130° C.

EXAMPLE 18

6-(2-Morpholino Ethyl)Benzothiazolinone, Hydrochloride

Using the procedure described in Example 11 but replacing 1-(2-methoxy phenyl) piperazine by morpholine, the product of the title is obtained.
Recrystallization in 95° strength alcohol.
Melting point: >260° C.

EXAMPLE 19

3-Methyl 6-(4-Morpholino Butyl)Benzothiazolinone,Hydrochloride

Using the procedure described in Example 8 but replacing 1-(2-methoxy phenyl) piperazine by morpholine, the product of the title is obtained.
Recrystallization in toluene.
Melting point: 171°-173° C.

According to the previous procedure the following are obtained:
7-{2-(4-(4-Fluoro Phenyl)-1-Piperazinyl]Ethyl}2,3-Dihydro 3-Oxo 1,4 Benzothiazine
7-{2-[4-(2-Methoxy Phenyl)-1-Piperazinyl]Ethyl}2,3-Dihydro 3Oxo 1,4 Benzothiazine
7-{2-[4-(2-Pyrimidyl)-1-Piperazinyl]Ethyl}2,3-Dihydro 3-Oxo 1,4 Benzothiazine
7-{2-[4-(2-Pyridyl)-1-Piperazinyl]Ethyl}2,3-Dihydro 3-Oxo 1,4 Benzothiazine
4-Methyl 7-{2-[4-(3-Trifluoromethyl Phenyl)Piperazin-1 yl]Ethyl}2,3-Dihydro 3-Oxo 1,4-Benzothiazine
4-Methyl 7-{2-[4-(2-Methoxy Phenyl)Piperazin-1 yl]Ethyl}2,3-Dihydro 3-Oxo 1,4-Benzothiazine
4-Methyl 7-{2-[4-(4-Fluoro Phenyl)Piperazin-1 yl]Ethyl}2, 3-Dihydro 3-Oxo 1,4-Benzothiazine
4-Methyl 7-{4-[4-(3-Trifluoromethyl Phenyl)Piperazin-1 yl]Butyl}2,3-Dihydro 3-Oxo 1,4-Benzothiazine 4-Methyl 7-{4-[4-(2-Methoxy Phenyl)Piperazin-1 yl]-Butyl}2,3-Dihydro 3-Oxo 1,4-Benzothiazine 4-Methyl 7-{4-[4-(4-Fluoro Phenyl)Piperazin-1 yl]-Butyl}2,3-Dihydro 3-Oxo 1,4-Benzothiazine 7-{4-[4-(3-Trifluoromethyl Phenyl)Piperazin-1 yl]-Butyl}2,3-Dihydro 3-Oxo 1,4-Benzothiazine 7-{4-[4-(2-Methoxy Phenyl)Piperazin-1 yl]Butyl}2,3-Dihydro 3-Oxo 1,4-Benzothiazine 7-{-[4-(4-Fluoro Phenyl)Piperazin-1 yl]Butyl}2,3-Dihydro 3-Oxo 1,4-Benzothiazine 6-{2-[4-(4-Fluoro Phenyl)Piperazin-1 yl]Ethyl}Benzothiazolinone 6-{4-[4-(4-Fluoro Phenyl)Piperazin-1 yl]Butyl}Benzothiazolinone 6-{2-[4-Phenyl Piperazin-1-yl]Ethyl}Benzothiazolinone and its 3-methylated compound.

6-{4-[4-Phenyl Piperazin-1-yl]Butyl}Benzothiazolinone and its 3-methylated compound.

7-{2-[4-Phenyl Piperazin-1-yl]Ethyl}2,3-Dihydro 3-Oxo Benzothiazine and its 4-methylated compound.

7-{4-[4-Phenyl Piperazin-1-yl]Butyl}2,3-Dihydro 3-Oxo Benzothiazine and its 4-methylated compound.

6-{2-[4-(4-Fluoro Phenyl)-1 Piperazinyl]Ethyl}2,3-Dihydro 3-Oxo 1,4-Benzothiazine 6-{2-[4-(2-Methoxy Phenyl)-1 Piperazinyl]Ethyl}2,3-Dihydro 3-Oxo 1,4-Benzothiazine 6-{2-[4-(3-Trifluoromethyl Phenyl)-1 Piperazinyl]Ethyl}2,3-Dihydro 3-Oxo 1,4-Benzothiazine 6-{2-[4-(2-Pyrimidyl)-1 Piperazinyl]Ethyl}2,3-Dihydro 3-Oxo 1,4-Benzothiazine Pharmacological Study of the Compounds of the Invention

EXAMPLE 20

In Vitro Affinity Test for 5-HT$_{1A}$, 5-HT2, D$_2$ and $\alpha_2$ Receptors

The in vitro affinity tests for 5-HT$_{1A}$, 5-HT$_2$, D2 and $\alpha_2$ receptors were carried out according to conventional binding techniques.

The results of these studies show that the compounds of the invention possess a IC$_{50}$ of the order of $10^{-10}$M with respect to 5-HT$_1$A receptors. In comparison, the IC50 compounds of EP 281309 is about $10^{-9}$M. This very great affinity is complemented by a very great selectivity.

The ratio 5HT$_1$A /5HT$_2$ is about from 300 to 600 that is to say greater from 11 to 26 that of compounds of EP 281309.

EXAMPLE 21

Acute Toxicity

The acute toxicity was assessed after oral administration of a dose of 650 mg.kg$^{-1}$ to batches of 8 mice (26 æ 2 grams). The animals were observed at regular intervals during the first day and daily during the two weeks following the treatment.

It is apparent that most of the compounds of the invention are completely non-toxic. Most of them cause no deaths after administration at a dose of 650 mg.kg$^{-1}$, and no disorders are generally observed after administration of this dose.

EXAMPLE 22

Study of Anxiolytic Acitivty—Pigeon Conflict Test

Six White Carneaux pigeons not previously used in experiments are trained to peck a Plexiglass key which is transilluminated by red or white lights. The response key is mounted on the front wall of the experimental chamber. The pigeons are brought to 85% of their normal weight before the beginning of the experiment, which is carried out using the method of successive approximations (Frester 1953). At the start, each peck of the key (illuminated with a red or white light) which exceeds a force of 0.15N permits access to a mixture of cereals via an automatic dispenser located under the key. After several days, the cereals are no longer delivered until the thirtieth peck on the key. When this response to the 30th strike is obtained, and when it occurs regularly, permitting the delivery of feed, the color of the light of the key is alternated every three minutes (from white to red and vice versa). The measurement of the level of response to the 30th strike remains operative during each light phase.

During this phase and throughout the experiment, a daily session is composed of 5 cycles of 3 minutes of each light sequence, these sequences being separated by a 30-second interval during which the luminous keys are extinguished and the responses have no effect. Consequently, a sequence lasts approximately 35 to 40 minutes. When these levels of responses are stable and identical for each color during a period of 5 days (this requires 3 to 4 weeks), every 30th response in one of the colored phases simultaneously brings about a release of feed and a brief (200-millisecond) and moderate (1.3 mA) electric shock delivered by electrodes placed on the pubic pones. The level of reponses is reduced at first, then returns to the initial value.

The administration of the products of the invention is carried out after a stable level of response is obtained over a period of 5 days.

The intramuscular injection of the products of the invention at a dose of 0.3 mg/kg$^{-1}$ brings about a significant increase in responses whether or not followed by electric shocks, demonstrating the anxiolytic activity of these products.

EXAMPLE 23

Study of Hypnotic Activity

Male IFFA-CREDO strain OF1 mice weighing on average 22 ±2 grams receive by esophageal intubation a solution consisting of gum arabic containing the test compound, namely 10 mg.kg$-1$, on the basis of 0.25 ml per 20 g of body weight. The time taken by the animal to fall asleep after being placed in dorsal decubitus and the duration of sleeping are noted. Pentobarbital is taken as a reference at a dose of 50 mg.kg$^{-1}$.

It is apparent that some compounds of the invention at a dose of 10 mg.kg$^{-1}$ have a hypnotic activity greater than that of pentobarbital at a dose of 50 mg.kg$-1$, taken as a reference.

EXAMPLE 24

Pharmaceutical Compositions

Tablets intended for the treatment of psychotic disorders, containing 2,5 mg of 3-methyl-6-{2-[4-(3-trifluoromethyl-phenyl)-1-piperazinyl]ethyl}benzothiazolinone hydrochloride.

| Preparation formula for 1,000 tablets | |
|---|---|
| 3-Methyl-6-{2-[4-(3-trifluoromethylphenyl)-1-piperazinyl]ethyl}benzothiazolinone hydrochloride | 2,5 g |
| Wheat starch | 15 g |
| Corn starch | 15 g |

| Preparation formula for 1,000 tablets | |
| --- | --- |
| Lactose | 65 g |
| Magnesium stearate | 2 g |
| Silica | 1 g |
| Hydroxypropylcellulose | 2 g |

We claim:

1. A compound selected from those of formula (I):

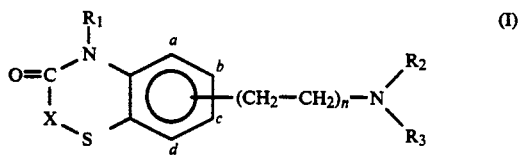

in which:

$R_1$ represents hydrogen or lower alkyl, n represents 1 or 2,

X represents $CH_2$ or a single bond, $R_2$ and $R_3$, together with the nitrogen atom which carries them, form a mono- or bicyclic heterocyclic system, each ring being five- or six-membered and optionally including in its carbon skeleton one or two hetero atoms selected from nitrogen, oxygen and sulfur, said ring being unsubstituted or substituted on a nitrogen atom present with lower alkyl, phenyl, phenyl (lower alkyl), pyridyl, or pyrimidinyl, or phenyl substituted with one or more lower alkyl, trifluoromethyl, or lower alkoxy groups or halogen atoms, or phenyl (lower alkyl) substituted on the phenyl ring with one or more lower alkyl, trifluoromethyl or lower alkoxy groups or halogen atoms, or pyridyl substituted with one or more lower alkyl, trifluoromethyl or lower alkoxy groups or halogen atoms, their enantiomers, diastereoisomers and epimers as well as their addition salts with a pharmaceutically-acceptable acid or a pharmaceutically-acceptable base when $R_1=H$.

2. A compound as claimed in claim 1 in which $R_2$ and $R_3$ together with the nitrogen atom which carries them form a piperazine ring substituted with phenyl, phenyl (lower alkyl), pyridyl, or pyrimidinyl or phenyl substituted with one or more lower alkyl, trifluoromethyl, or lower alkoxy groups or halogen atoms, or phenyl (lower alkyl) substituted on the phenyl ring with one or more lower alkyl, trifluoromethyl or lower alkoxy groups or halogen atoms, or pyridyl substituted with one or more lower alkyl, trifluoromethyl or lower alkoxy groups or halogen atoms, their enantiomers, diastereoisomers and epimers as well as their addition salts with a pharmaceutically-acceptable acid or a pharmaceutically-acceptable base when $R_1=H$.

3. A compound as claimed in claim 1 in which $R_2$ and $R_3$ together with the nitrogen atom which carries them form a morpholino ring as well as addition salts thereof with a pharmaceutically-acceptable acid and/or a pharmaceutically-acceptable base when $R_1=H$.

4. A compound as claimed in claim 1 in which X represents a single bond, its enantiomers, epimers and diastereoisomers as well as its addition salts with a pharmaceutically-acceptable acid or a pharmaceutically-acceptable base when $R_1=H$.

5. A compound as claimed in claim 1 in which X represents a $CH_2$ group, its enantiomers, epimers and diastereoisomers as well as its addition salts with a pharmaceutically-acceptable acid or a pharmaceutically-acceptable base when $R_1=H$.

6. A compound as claimed in claim 1 in which the group $(CH_2-CH_2)_n-NR_2R_3$ is at position c, its enantiomers, epimers and diastereoisomers as well as its addition salts with a pharmaceutically-acceptable acid or a pharmaceutically-acceptable base when $R_1=H$.

7. A compound as claimed in claim 1 in which the group $(CH_2-CH_2)_n-NR_2R_3$ is at position d, its enantiomers, epimers and diastereoisomers as well as its addition salts with a pharmaceutically-acceptable acid or a pharmaceutically-acceptable base when $R_1=H$.

8. A compound as claimed in claim 1 which is selected from 6-{2-[4-(3-trifluoromethylphenyl)-1-piperazinyl]ethyl}benzothiazolinone, its 3-methylated compound, and addition salts thereof with a pharmaceutically-acceptable acid or base.

9. The compound as claimed in claim 1 which is selected from 6-{2-[4-(2-methoxyphenyl)-1-piperazinyl]ethyl}benzothiazolinone, its 3-methylated compound, and addition salts thereof with a pharmaceutically-acceptable acid.

10. A compound as claimed in claim 1 which is selected from 6-{2-[4-(4-fluorophenyl)-1-piperazinyl]ethyl}benzothiazolinone, its 3-methylated compound, and addition salts thereof with a pharmaceutically-acceptable acid or base.

11. A compound as claimed in claim 1 which is selected from 6-{4-[4-(2-methoxyphenyl)-1-piperazinyl]butyl}benzothiazolinone, its 3-methylated compound, and addition salts thereof with a pharmaceutically-acceptable acid or base.

12. A compound as claimed in claim 1 which is selected from 7-{2-[4-(3-trifluoromethyl phenyl)-1-piperazinyl]ethyl}2,3-dihydro 3-oxo 1,4-benzothiazine and addition salts thereof with a pharmaceutically-acceptable acid or base.

13. A compound as claimed in claim 1 which is selected from 3-methyl-6-{2-[4-(2-pyrimidyl)-1-piperazinyl]ethyl}benzothiazolinone and addition salts thereof with a pharmaceutically-acceptable acid.

14. A compound as claimed in claim 1 which is selected from 6-{4-[4-(3-trifluoromethyl phenyl)-1-piperazinyl]butyl}benzothiazolinone, the corresponding 3-methylated compound, and addition salts thereof with a pharmaceutically-acceptable acid or base.

15. A compound as claimed in claim 1 which is selected from 6-{4-[4-(4-fluoro phenyl)-1-piperazinyl]butyl} benzothiazolinone, the corresponding 3-methylated compound, and addition salts thereof with a pharmaceutically-acceptable acid or base.

16. A compound as claimed in claim 1 which is selected from 7-{2-[4-aryl-1-piperazinyl]ethyl}2,3-dihydro-3-oxo-1,4 benzothiazine in which aryl denotes a phenyl group, a 2-methoxy phenyl group, a 3-trifluoromethyl group, a 4-fluoro phenyl group, the corresponding 4-methylated compounds, and addition salts thereof with a pharmaceutically-acceptable acid or base.

17. A compound as claimed in claim 1 which is selected from 7-{4-[4-aryl-1-piperazinyl]butyl}2,3-dihydro-3-oxo-1,4 benzothiazine in which aryl denotes a phenyl group, a 2-methoxy phenyl group, a 4-fluoro phenyl group, a 3-trifluoromethyl group, the corresponding 4-methylated compounds, and addition salts thereof with a pharmaceutically-acceptable acid or base.

18. A compound as claimed in claim 1 which is selected from 6-{2-[4-phenyl-1-piperazinyl]ethyl}benzothiazolinone, the corresponding 3-methylated compound, and addition salts thereof with a pharmaceutically-acceptable acid or base.

19. A compound as claimed in claim 1 which is selected from 6-{4-[4-phenyl-1-piperazinyl]butyl}benzothiazolinone, the corresponding 3-methylated compound, and addition salts thereof with a pharmaceutically-acceptable acid.

20. A compound as claimed in claim 1 which is selected from 6-(2-morpholino ethyl) benzothiazolinone and addition salts thereof with a pharmaceutically-acceptable acid or base.

21. A compound as claimed in claim 1 which is selected from 3-methyl 6-(4-morpholino butyl) benzothiazolinone and addition salts thereof with a pharmaceutically-acceptable acid.

22. A pharmaceutical composition containing as active principle at least one compound as claimed in claim 1 in combination with one or more pharmaceutically-acceptable excipients or vehicles.

23. A method for treating a mammal afflicated with pain or arterial hypertension comprising the step of administering to the said living animal an amount of a compound of claim 1 which is effective for alleviation of said condition.

* * * * *

UNITED STATES PATENT AND TRADEMARK OFFICE
CERTIFICATE OF CORRECTION

PATENT NO. : 5,234,924
DATED : August 10, 1993
INVENTOR(S) : Thierry Taverne, Isabelle Lesieur, Patrick Depreux, Daniel H. Caignard, Béatrice Guardiola, Gérard Adam, and Pierre Renard It is certified that error appears in the above-indentified patent and that said Letters Patent is hereby corrected as shown below:

Title page, [30]; "90 11866" should read -- 90.11866 --.
Col. 1, line 41; "inconvenient" should read -- inconvenience --.
Col. 1, line 52; "Applications" should read -- Application --.
Col. 6, line 45; "(3H) 1 NCH$_3$" should read -- (3H) ; NCH$_3$ --.
Col. 7, line 2; delete "Oromethylphenyl)-1-Piperazinyl)"
Col. 7, line 3; delete "Ethyl)".
Col. 7, line 19; "Co" should read -- CO --.
Col. 7, line 23; "singlet : (3H) : NCH$_3$" should read -- singlet ; (3H) ; NCH$_3$ --.
Col. 8, line 9; insert a bracket -- [ -- before the "4" and move the "E" at the end of the line to the beginning of line 10 ahead of "thyl".
Col. 8, line 10; delete the hyphen before "Benzothiazolinone".
Col. 9, line 32; "Re" should be on the next line to form the word --Recrystallisation--.
Col. 10, line 22; delete the "b".
Col. 10, line 25; the parenthesis -- ) -- between "Piperazinyl" and "Butyl" should be a bracket -- ] --.
Col. 10, line 53; "7-{2-(4-(4-Fluoro" should read -- 7-{2-[4-(4-Fluoro --.
Col. 10, line 56; insert a hyphen between "3" and "Oxo".
Col. 12, line 66; "2,5 g" should read -- 2.5 g --.
Col. 13, line 45; insert a comma after "pyrimidinyl".

UNITED STATES PATENT AND TRADEMARK OFFICE
CERTIFICATE OF CORRECTION

PATENT NO. : 5,234,924

DATED : August 10, 1993

INVENTOR(S) : Thierry Taverne, et al

It is certified that error appears in the above-indentified patent and that said Letters Patent is hereby corrected as shown below:

Col. 16, line 11; change "living animal" to --mammal--.

Signed and Sealed this

Fifth Day of July, 1994

*Attest:*

BRUCE LEHMAN

*Attesting Officer*     *Commissioner of Patents and Trademarks*